United States Patent [19]

Reetz et al.

[11] Patent Number: 4,990,669

[45] Date of Patent: Feb. 5, 1991

[54] OPTICALLY ACTIVE ALPHA-AMINO ALDEHYDES, PROCESS FOR THE PREPARATION THEREOF, AND THE USE THEREOF FOR THE STEREOSELECTIVE PREPARATION OF OPTICALLY ACTIVE BETA-AMINO ALCOHOLS

[75] Inventors: Manfred T. Reetz; Mark W. Drewes, both of Marburg, Fed. Rep. of Germany

[73] Assignee: Bayer Aktiengesellschaft, Leverkusen, Fed. Rep. of Germany

[21] Appl. No.: 172,046

[22] Filed: Mar. 23, 1988

[30] Foreign Application Priority Data

Apr. 8, 1987 [DE] Fed. Rep. of Germany ....... 3711911

[51] Int. Cl.$^5$ ................. C07C 237/10; C07C 211/27; C07D 403/06; C07D 209/44
[52] U.S. Cl. .................................... 564/391; 548/336; 548/342; 548/455; 548/470; 548/472; 548/473; 548/511; 564/152; 564/153; 564/154; 564/155; 564/162; 564/163; 564/164; 564/165; 564/340; 564/342; 564/344; 564/374; 564/389; 564/392; 564/453; 564/502
[58] Field of Search ............... 564/389, 391, 392, 374, 564/433, 462, 457, 502, 153, 154, 152, 162, 163, 164, 165, 342, 344; 548/342, 455, 468, 511

[56] References Cited

PUBLICATIONS

Solomons, *Organic Chemistry*, 2nd Ed., John Wiley and Sons, N.Y. (1980), pp. 705, 706 and 878–881.
Chemical Abstracts, vol. 81, No. 23 (1974), Abst. No. 152575b.
Chemical Abstracts Formula Index ($C_{16}$-Z), vol. 81 (1974), p. 1926f, "$C_{41}H_{43}NO_5$".
Reetz et al., "Stereoselective Synthesis of β-Amino Alcohols, etc.", *Chem. Abst* (1987), 108: 37185p.

Gent et al., "The Allyl Ether as a Protecting Group, Etc", *J. Chem. Soc.*, Perkin Trans. 1, (12), 1446–55.
Duhamel et al., "Effect of Steric Factors on the Isomerization of α-Amino Aldehydes, etc.", CA, vol. 73, 3296u (1970).
Agnew. Chem 99 (1987) (11), pp. 1186–1188, Stereoselektive Synthese von Beta-Aminoalkoholen aus Optisch Aktiven Alpha-Aminosauren.
Agnew Chem. 96, pp. 542–555; Chelat- oder Nicht Kontrolle bei Additionsreaktiinen von chiralen alpha- und Beta-Alkoxycarbonyl-Verbindungen (1984).

*Primary Examiner*—Richard L. Raymond
*Assistant Examiner*—Peter G. O'Sullivan
*Attorney, Agent, or Firm*—Sprung Horn Kramer & Woods

[57] ABSTRACT

The invention relates to new optically active α-amino aldehydes of the formulae

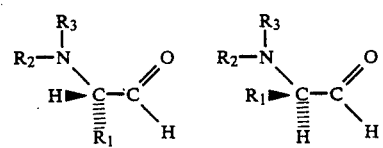

in which
$R_1$ represents an optionally substituted alkyl, alkenyl, aralkyl or aryl radical, and
$R_2$ and $R_3$, independently of one another, denote an optionally substituted alkyl, alkenyl, cycloalkyl or aralkyl group, together form an optionally substituted phenylene-(1,2)-bis-methylene radical, or $R_2$ is an optionally substituted, alkyl, cycloalkyl or aralkyl radical, and $R_3$ forms together with $R_1$ a 1,3-propylene radical.

a process for the preparation thereof, and the use thereof for the stereoselective preparation of optically active β-amino alcohols.

4 Claims, No Drawings

OPTICALLY ACTIVE ALPHA-AMINO ALDEHYDES, PROCESS FOR THE PREPARATION THEREOF, AND THE USE THEREOF FOR THE STEREOSELECTIVE PREPARATION OF OPTICALLY ACTIVE BETA-AMINO ALCOHOLS

The invention relates to new, optically active α-amino aldehydes having a protected amino group, process for the preparation thereof, and the use thereof for the stereoselective preparation of optically active β-amino alcohols.

Optically active α-amino aldehydes having a protected amino group are important intermediates for the preparation of optically active β-amino alcohols. The optically active δ-amino alcohols are in turn important intermediates for the preparation of biologically active compounds, specifically both naturally occurring and synthetically prepared active compounds. In many cases these active compounds take the form of di- or oligopeptides which contain optically active β-amino alcohols as chain members, for example renin inhibitors having a reducing effect on blood pressure (see CA 104, (1986) 19 822 g and Tetrahedron Letters, vol. 27, No. 21, pages 2337-2340, (1986)); dietetic sweeteners (see EP-A 1,0068,551) and of bestatin derivatives which intensify the antitumour efficacy of bleomycin (see DE-OS (German Published Specification) 2,632,396).

Because of the great importance of the optically active α-amino aldehydes as intermediates for the preparation of optically active β-amino alcohols from naturally occurring amino acids (=optically active α-amino acids), there has been intensive work on the preparation of the optically active α-amino aldehydes and their further reaction to give the optically active amino alcohols. It is particularly important in this indicated reaction sequence that all the reaction steps, that is to say both the reduction of the optically active amino acids to give the α-amino aldehydes and the conversion of the α-amino aldehydes into the β-amino alcohols take place with retention of the configuration at the α-C atom and stereoselectively in the formation of the new optically active β-C atom. Since the configurational stability of the α-amino aldehydes and the stereoselectivity of their reactions with organometallic compounds and enolates to give the corresponding β-amino alcohols are substantially determined by the protective group present on the nitrogen of the α-amino aldehyde, a very wide variety of protective groups have been used to block the amino group of the α-amino aldehydes. However, the configurational stabilities and stereoselectivities achieved with these protective groups used hitherto are inadequate, as shown by the mixtures of diastereomeric β-amino alcohols obtained on reaction of the N-protected optically active α-amino aldehydes, and the optical purity of the individual diastereomeric β-amino alcohols.

The following specific protective groups have hitherto been used for blocking the amino group of the optically active α-amino acids and of the optically active α-amino aldehydes prepared therefrom:

1. The tertiary butoxycarbonyl group (Boc): The α-amino aldehydes having an amino group protected by a Boc group have the disadvantage that they are not always configurationally stable and provide mixtures of the disteromeric β-amino alcohols on reaction with organometallic compounds and enolates (see the corresponding statements in Tetrahedron Letters loc. cit. and J. Am. Chem. Soc. 1987, 109, pages 236-239).

2. The triphenylmethyl group (trityl group): The α-amino aldehydes protected on the nitrogen by a trityl group have only inadequate configurational stability and, on reaction with organometallic compounds and enolates, provide mixtures of the two diastereomeric alcohols (see the statements in Tetrahedron Letters loc. cit.).

3. The 9-(9-phenylfluorenyl) group: Although the α-amino aldehydes protected on the nitrogen by the 9-(9-phenylfluorenyl) group have improved configurational stability, mixtures of the two diastereomeric β-amino alcohols are formed on reaction with organometallic compounds or enolates (see J. Am. Chem. Soc. 1987, 109, pages 136-239).

It has now been found that α-amino aldehydes having an amino group which is completely protected by alkyl, alkenyl, cycloalkyl or aralkyl groups, that is to say is peralkylated, have a surprisingly high configurational stability and react with organometallic compounds and enolates stereoselectively to give the corresponding β-amino alcohols.

Hence the invention relates to optically active α-amino aldehydes which are substituted on the nitrogen and are of the formulae

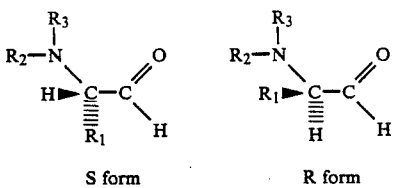

in which

R$_1$ represents an optionally substituted alkyl, alkenyl, aralkyl or aryl radical, and R$_2$ and R$_3$, independently of one another, denote an optionally substituted alkyl, alkenyl, cycloalkyl or aralkyl group, preferably an optionally substituted benzyl group, together form an optionally substituted phenylene-(1,2)-bis-methylene radical, or R$_2$ is an optionally substituted alkyl, cycloalkyl or aralkyl radical, preferably an optionally substituted benzyl radical, and R$_3$ forms together with R$_1$ a propylene-1,3 radical.

For simplicity, the α-amino aldehydes of the formula I within the scope of the present invention are designated peralkylated amino aldehydes. Because the benzyl groups can be eliminated particularly easily, the perbenzylated amino aldehydes of the formula I are preferred.

Examples of optionally substituted alkyl radicals for R$_1$ which may be mentioned are: C$_1$-C$_{12}$-alkyl radicals such as the methyl, ethyl, iso-propyl, butyl, sec.-butyl, iso-butyl, amyl and hexyl radicals; suitable and preferred substituents for the alkyl radicals are the amino, hydroxyl, benzyloxy, benzylmercapto, carbamyl groups, or the imidazolyl-4 group or the indolyl-3 group which are optionally substituted on the N. Examples of optionally substituted alkyl radicals which may be mentioned are: the benzyloxymethyl, benzylthiomethyl, 1-benzyloxyethyl, 2-methylthioethyl, carbamoylmethyl, 2-carbamoylethyl, 3-(N,N-dibenzylamino)-propyl, 4-(N,N-dibenzylamino)butyl, the (imidazolyl-4)-methyl and the (indolyl-3)-methyl radical.

An example of an optionally substituted alkenyl radical which may be mentioned is the vinyl radical.

Examples of optionally substituted aralkyl radicals which may be mentioned are: the benzyl radical and benzyl radicals substituted by $C_1$–$C_4$-alkyl, $C_1$–$C_4$-alkoxy, benzyloxy or halogen atoms, such as the 2- and 4-methylbenzyl radical, the 4-methoxybenzyl and the 4-benzyloxybenzyl radical.

Examples of optionally substituted aryl radicals which may be mentioned are the phenyl radical and phenyl radicals substituted by OH, $C_1$–$C_4$-alkoxy and $C_1$–$C_4$-alkyl groups, such as the 4-hydroxyphenyl radical, the 4-methoxyphenyl radical and the 2-methyl and 4-methoxyphenyl radical.

Optionally substituted alkyl radicals which may be mentioned for $R_2$ and $R_3$ are $C_1$–$C_{12}$-alkyl radicals such as the methyl, ethyl, n-propyl, i-butyl, 2-ethylhexyl and the dodecyl radical, and $C_1$–$C_{12}$-alkyl radicals substituted by CO or OH groups, and optionally substituted alkenyl radicals which may be mentioned are, in particular, the allyl radical; and optionally substituted cycloalkyl radicals which may be mentioned are the cyclopentyl, cyclohexyl, methyl-cyclohexyl and dimethylcyclohexyl radical.

Optionally substituted benzyl radicals which may be mentioned for $R_2$ and $R_3$ are the benzyl and phenylene-(1,2)-bis-methylene radicals each of which are substituted by $C_1$–$C_4$-alkyl groups, $C_1$–$C_4$-alkoxy and benzyloxy groups or by halogen atoms; for example the 2- and 4-methylbenzyl radical, the 2- and 4-methoxybenzyl radical and the α-methylbenzyl radical.

The invention furthermore relates to a process for the preparation of the optically active amino aldehydes of the formula I which are peralkylated on the N; the process is characterized in that optically active amino acids, or their esters, which are peralkylated on the nitrogen, of the formulae

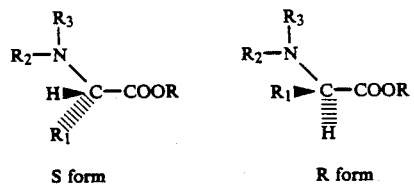

S form      R form in which
$R_1$, $R_2$ and $R_3$ have the meaning indicated under formula I, and
R represents hydrogen, an alkyl or aralkyl radical, are reduced by processes known per se to give the α-amino aldehydes of the formula I which are peralkylated on the nitrogen.

Examples of known processes for the reduction of α-amino carboxylic acids which are protected on the N to give the α-amino aldehydes which are protected on the N are:

(a) the reduction of the α-amino carboxylic acids or their esters with lithium aluminium hydride and oxidation of the β-amino alcohols protected on the nitrogen, which are obtained in this way, with dimethyl sulphoxide/oxalyl chloride or chromium trioxide/pyridine to give the α-amino aldehydes protected on the N;

(b) the reduction of the amino carboxylic acids or their esters with diisobutylaluminium hydride to give the α-amino aldehydes protected on the N.

α-Amino acids peralkylated on the N and their preparation are known (see Beilstein E IV, vol. 12, pages 2287, 2295–2297; System No. 1699). The optically active α-amino acids peralkylated on the N are prepared analogously by alkylation of corresponding optically active α-amino acids, for example naturally occurring amino acids.

A particularly advantageous embodiment of the process according to the invention for the preparation of the amino aldehydes of the formula I comprises, in one step, alkylation of the optically active α-amino acids by reaction with alkyl, alkenyl, cycloalkyl or aralkyl halides, preferably with benzyl halides such as benzyl chloride or—particularly preferably—with benzyl bromide, on the nitrogen and conversion of the carboxyl group into a carboxylic ester group.

Preferably are used as the optically active α-amino acids the in nature occurring optically active α-amino acids.

The amino acid esters peralkylated on the N which are obtained in this way are then converted, as indicated above, into the peralkylated amino aldehydes of the formula I, according to the invention, in a known manner either by reduction with lithium aluminium hydride and oxidation with dimethyl sulphoxide/oxalyl chloride or by reduction with diisobutylaluminium hydride.

The invention furthermore relates to the use of the optically active α-amino aldehydes of the formula I, according to the invention, for the preparation of optically active β-amino alcohols of the formulae

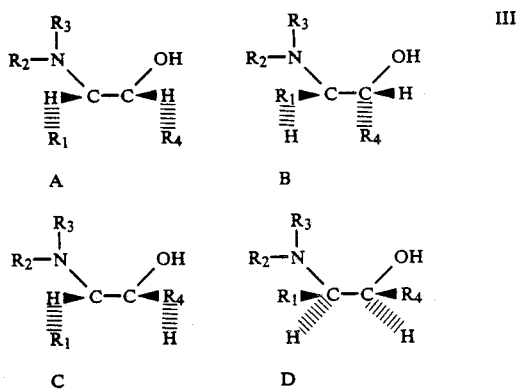

in which
$R_1$, $R_2$ and $R_3$ have the meaning indicated under formula I, and
$R_4$ represents an optionally substituted alkyl, alkenyl, alkynyl, aralkyl, aryl or heteroaryl radical or the CN group.

Examples of substituents for the alkyl, alkenyl, alkynyl, aralkyl, phenyl and heteroaryl radicals which may be mentioned are protected hydroxyl, mercapto and amino groups, as well as sulphoxide, sulphone, nitro and cyano groups.

To prepare the optically active β-amino alcohols of the formula III, the optically active α-amino aldehydes of the formula I, according to the invention, are reacted in a manner known per se (see, for example, Angew. Chem. 96, pages 542–555, (1984)) with organometallic compounds or enolates in an organic solvent which is inert under the reaction conditions.

Examples of organometallic compounds which may be mentioned are: organometallic compounds in which the metal atom is bonded only to organic groups (so-called homogeneous organometallic compounds) such as alkyl-, vinyl-, alkynyl-, aryl- or heteroaryl-lithium, for example methyl-, methoxymethyl-, cyanomethyl-, phenylsulphonylmethyl-, N,N-dialkylaminomethyl-, butyl-, allyl-, 3-alkoxyallyl-, vinyl-, 1-ethoxyvinyl- and phenyl-lithium; also 2-Li-furan, 2-Li-4-methyl-1,3-thiazole, 5-Li-1-methylpyrazole, 2-Li-pyridine and α-picolyl-Li; nitromethylsodium; dialkyl- or dialkenyl-zinc, for example dimethyl or diallyl-zinc; dialkylmagnesium for example dimethylmagnesium and silanes such as allyltrimethylsilane.

Organometallic compounds in which the metal atom is bonded not only to organic groups but also to other groups, atoms or ions (so-called mixed organometallic compounds), for example Grignard and Grignard-analogous compounds such as alkyl-, alkenyl-, alkynyl-, aralkyl- or aryl-magnesium halides such as methyl-magnesium chloride or iodide, allyl-magnesium bromide, benzyl-magnesium iodide, phenyl-magnesium bromide, alkyl-, alkenyl-, alkynyl-, aralkyl- or aryl-manganese halides such as $CH_3MnBr$, alkyl-, alkenyl-, alkynyl-, aralkyl- or aryl-titanium chlorides or alkoxylates such as $CH_3TiCl_3$ or $CH_3Ti(OC_3H_7i)_3$, as well as mixed silanes such as $(CH_3)_3SiCN$.

Some of the organometallic compounds, for example dimethyl- or dibutylzinc, as well as silanes such as allyltrimethylsilane, are used in combination with fluoride ions or Lewis acids, for example $(CH_3)_2Zn/TiCl_4$, allyltrimethylsilane/$SnCl_4$, $(CH_3)_3SiCN/F^-(NR'_4)^+$, $(CH_3)_3SiCN/BF_3$ or $(CH_3)_3SiCN/MgBr_2$.

Examples of enolates which may be mentioned are: lithium, boron and titanium enolates of optionally substituted carboxylic esters (for example ethyl acetate, ethyl benzyloxy acetate, ethyl α-isocyanoacetate or ethyl N,N-dibenzylaminoacetate) and ketones, as well as the O-trimethylsilylketene ketals of these carboxylic esters and O-trimethylsilyl enol silanes of the ketones. Enolates within the scope of the present invention are also understood to be enolate-analogous compounds such as α-lithiated imines or lithiated bis-lactim ethers.

O-Trimethylsilylketene ketals and O-trimethylsilyl enol silanes are used in combination with Lewis acids such as $BF_3$, $MgBr_2$ or $SnCl_4$.

These addition reactions take place with high stereoselectivity. The resulting β-amino alcohols of the formula III consist on average of 90 to 97% of a single diastereomer and now contain only about 10 to 3% of the other diastereomer.

The optical purity of the β-amino alcohols of the formula III obtained by reaction of the α-amino aldehydes of the formula I, according to the invention, with organometallic compounds and enolates have been determined by $^{13}C$ NMR spectroscopic investigation of the esters obtained by O-acylation of the amino alcohols with (+)- and (-)-α-methoxy-α-(trifluoromethyl)-phenylacetyl chloride. According to this, the optical purity of the individual diastereomers is at least 98%, that is to say no racemization worthy of note takes place at the α-C atom either during the preparation or during the reactions of the aldehydes I.

It has been found that reaction of the peralkylated amino aldehydes of the formula I, according to the invention, with organometallic compounds and enolates takes place stereoselectively with the formation of the non-chelate-controlled diastereomeric β-amino alcohols of the formulae IIIA or IIID, depending on whether the S or the R form of the α-amino aldehydes of the formula I has been used, whereas the reaction with organometallic compounds in combination with Lewis acids such as $TiCl_4$ or $SnCl_4$ results in the formation of the chelate-controlled diastereomeric β-amino alcohols of the formulae IIIB or IIIC. Only the reaction of $(CH_3)_3SiCN$ in combination with zinc halides or $BF_3$ results in the formation of diastereomeric β-amino alcohols of the formulae IIIA or IIID.

The reaction of the α-amino aldehydes of the formula I, according to the invention, with organometallic compounds can be carried out in a manner known per se (see, for example, the statements in J. Am. Chem. Soc., vol. 109, No. 1, 1987, pages 237–238).

The N,N-disubstituted β-amino alcohols of the formula III are suitable as catalysts for the enantioselective addition of diethylzinc onto aldehydes described in Chem Comm. (ICCCAT) (6) pages 467/468 (1987).

The benzyl groups can be eliminated from the βamino alcohols of the formula III in a manner known per se by catalytic hydrogenation (hydrogenolysis). The hydrogenolysis is preferably carried out with Pd black/charcoal using formic acid as hydrogen donor. The formamides initially formed in the hydrogenolysis are then hydrolysed either with alkali by addition of bases or—preferably—with acid by addition of dilute hydrochloric acid in the presence of silica gel.

EXAMPLE 1

(a) 10 g (=42 mmol) of alanine, 9.0 g (=224 mmol) of NaOH and 46.4 g (=336 mmol) of $K_2CO_3$ are dissolved in 100 ml of 5% strength ethanol. The solution is heated at the reflux temperature for 10 minutes and then 61.3 g (=358 mmol) of benzyl bromide are added. The reaction mixture is heated at the reflux temperature for 1 hour. The reaction mixture is then cooled, and the ethanol is removed by distillation in vacuo. The remaining aqueous solution is extracted with ether. The combined ether extracts are washed with saturated brine and dried over $MgSO_4$, and ether is removed in vacuo. The residue is purified by chromatography on a silica gel column (PE/EtOAc; 98:2). 27.8 g (=69% of theory) of benzyl S-α-(N,N-dibenzylamino)propionate are obtained in the form of a colourless oil.

With the same procedure and using 42 mmol of phenylalanine or 42 mmol of proline, 42 mmol of leucine or 42 mmol of valine in place of the 42 mmol of alanine there were obtained in comparable yields and also in the form of colourless oils:

(a1) benzyl S-α-(N,N-dibenzylamino)-β-phenylpropionate, (a2) benzyl S-(N-benzylamino)pyrrolidine-(2)-carboxylate, (a3) benzyl S-α-(N,N-dibenzylamino)-β-4-methylpentanecarboxylate and (a4) benzyl S-α(N,N-dibenzylamino)-3-methylbutanecarboxylate.

(b) (α) A solution of 20.2 g (=56 mmol) of benzyl S-α (N,N-dibenzylamino)propionate in 20 ml of ether is added dropwise, while stirring and cooling at 0° C., to a suspension of 2.56 g (=67 mmol) of lithium aluminium hydride in 75 ml of ether. After addition is complete, the cooling bath is removed, and the reaction mixture is stirred at room temperature for 2 hours. The reaction mixture is then hydrolysed by successive addition of 3 ml of $H_2O$, 3 ml of 15% strength sodium hydroxide solution and 9 ml of $H_2O$. The resulting hydroxides are filtered off and extracted twice by boiling with ether. After removal of the organic layer from the aqueous filtrate the latter is extracted several times with ether. The combined extracts are dried over magnesium sulphate and then concentrated in vacuo. The residue is purified by chromatography on a silica gel column (petroleum ether/ethyl acetate; 95:5). 10.4 g (=73% of theory) of S-2-(N,N-dibenzylamino)propanol are obtained in the form of white crystals (melting point 39° C.).

S-2-(N-Dibenzylamino)-3-phenyl-propanol, S-(N-benzylamino)-(2)-hydroxymethylpyrrolidine, S-2-(N,N-dibenzylamino)-4-methyl-1-pentanol and S-2-(N,N-dibenzylamino)-3-methyl-1-butanol were obtained in the same way by reduction of benzyl S-α-(N,N-dibenzylamino)-β-phenyl-propionate, of benzyl S-(N-benzylamino)pyrrolidine-(2)-carboxylate, of benzyl S-α-(N,N-dibenzxylamino)-4-methyl-pentanecarboxylate and of benzyl S-α(N,N-dibenzylamino)-3-methylbutanecarboxylate respectively.

(β) 301 mg (=3.92 mmol) of dimethyl sulphoxide are added dropwise to a solution of 270 mg (=2.11 mmol) of oxalyl chloride in 10 ml of methylene chloride which has been cooled to −60° C. The solution is stirred for 5 minutes, and then 500 mg (=2 mmol) of S-2-(N,N-dibenzylamino)propanol are added dropwise. The reaction mixture is stirred at −60° C. for 30 minutes, and then 0.99 g (=9.8 mmol) of triethylamine is added. The reaction mixture is stirred for 15 minutes and then warmed to room temperature. The methylene chloride solution is washed with 1.5% strength hydrochloric acid and then with 5% strength sodium carbonate solution and is dried over magnesium sulphate, and then methylene chloride is removed in vacuo.

0.44 g (=88% of theory) of S-α-(N,N-dibenzylamino)propionaldehyde is obtained in the form of a yellow oil. The compound can be used without further purification for the addition reactions which are described below.

In the same way S-2-(N,N-dibenzylamino)-3-phenyl-1-propanol, S-2-(hydroxymethyl)-(N-benzylamino)pyrrolidine, S-2-(N,N-dibenzylamino)-4-methyl-1-propanol and S-2-(N,N-dibenzylamino)-3-methyl-1-butanol were also oxidized to S-2-(N,N-dibenzylamino)-β-phenylpropionaldehyde, to S-(N-benzylamino) pyrrolidine-(2)-aldehyde, to S-2-(N,N-dibenzylamino)-4-methyl-pentanal and to S-2-(N,N-dibenzylamino)-3-methylbutanal, respectively.

(c) (α) A solution of 1 g (=4 mmol) of S-α-(N,N-dibenzylamino)propionaldehyde in 3 ml of ether is added dropwise to a solution of 4.8 mmol of methylmagnesium iodide in 4 ml of ether at 0° C. After the reaction mixture has been stirred for 1 hour, it is hydrolysed by addition of 8 ml of saturated ammonium chloride solution, the organic phase is separated off, and the aqueous phase is extracted with ether. The combined ethereal phases are washed with brine and dried over magnesium sulphate. The residue remaining after the ether has been removed by distillation is purified by chromatography. 925 mg (=87% of theory) of (2R,3S)-3-(N,N-dibenzylamino)-2-propanol are obtained in the form of white crystals of melting point 76°-77° C.

(β) A solution of 1.2 mmol of dimethylzinc in 10 ml of dry methylene chloride is stirred at −50° C. with 2.37 mmol of titanium tetrachloride. After the solution has been stirred for 45 minutes it is cooled to −78° C., and 2.3 mmol of S-α-(N,N-dibenzylamino)propionaldehyde are added. The reaction mixture is allowed to reach −40° C., is stirred at this temperature for 3 hours and is then poured onto water. The organic phase is separated off, and the aqueous phase is extracted with methylene chloride. The combined methylene chloride phases are washed with saturated sodium bicarbonate solution and dried over magnesium sulphate. After the methylene chloride has been removed by distillation, 523 mg (=82% of theory) of (2S,3S)-3-(N,N-dibenzylamino)-2-propanol are obtained in the form of an analytically pure oil. Determination of the diastereomer ratio by $^{13}C$ NMR spectroscopy showed a diastereomer ratio of 94:6.

(γ) A solution of 4 mmol of S-α-(N,N-dibenzylamino)propionaldehyde in 5 ml of ether is added to a solution of 4 mmol of phenylmagnesium bromide in 5 ml of ether at 0° C. After the reaction mixture has been stirred for 2 hours, saturated ammonium chloride solution is added. The organic phase is separated off, and the aqueous phase is extracted with ether. The combined ethereal phases are washed with brine. After drying over magnesium sulphate and removal of the solvent, 1.11 g (=85% of theory) of (1R,2S)-1-phenyl-2-(N,N-dibenzylamino)-1-propanol are obtained in the form of a yellow, analytically pure oil. This oil is identical to N,N-dibenzylaminonorephedrine.

To remove the benzyl group, 3.9 mmol of (1R,2S)-1-phenyl-2-(N,N-dibenzylamino)-1-propanol are dissolved in 5 ml of methanol. This solution is added to a mixture of 40 ml of methanol, 10.6 g of formic acid and 50 mg of palladium black. The air is displaced from the reaction vessel using hydrogen. After hydrogenation for 1 hour, the palladium catalyst is filtered off, and the solution is concentrated in vacuo. The residue is taken up in 10 ml of methanol and stirred with 1 g of silica gel and 5 drops of concentrated hydrochloric acid at room temperature for 1 hour. The residue obtained after removal of the silica gel by filtration and concentration of the filtrate is purified by chromatography. 243 mg (=60% of theory) of analytically pure norephedrine are obtained.

(δ) 2 mmol of methyl acetate are added dropwise to a solution of 2 mmol of lithium diisopropylamide in 25 ml of tetrahydrofuran at −78° C. After stirring for 15 minutes, a solution of 2 mmol of S-α-(N,N-dibenzylamino)propionaldehyde in 3 ml of tetrahydrofuran is added to the enolate solution obtained in this way. The reaction mixture is stirred for 15 minutes and then added to saturated sodium bicarbonate solution. The organic phase is separated off, and the aqueous phase is extracted several times with ether. The combined organic phases are washed and dried over magnesium sulphate. After the solvent has been removed by distillation, 529 mg (=82% of theory) of methyl (3R,4S)-3-hydroxy-4-(N,N-dibenzylamino)pentanoate are obtained in the form of an analytically pure oil.

Table 1 which follows lists the β-amino alcohols which were prepared according to the invention and which were obtained on addition of the agents indicated in Table 1 onto S-α-(N,N-dibenzylamino)propionaldehyde. Table 1 also indicates the yields and the diastereomer ratio in which the relevant β-amino alcohols were obtained.

Table 2 lists the β-amino alcohols which were obtained on addition of the nucleophilic agents indicated in Table 2 onto S-α-(N,N-dibenzylamino)-β-phenylpropionaldehyde.

Table 3 lists the β-amino alcohols which were obtained on addition of the nucleophilic agents indicated in Table 3 onto S-α-(N,N-dibenzylamino)-β-isopropylpropionaldehyde.

Table 4 lists the β-amino alcohols which were obtained on addition of the nucleophilic agents indicated in Table 4 onto S-α-(N,N-dibenzylamino)-4-methylpentanal.

TABLE 1

| Agent | Yield [% of theory] | R$_4$ | (C$_6$H$_5$CH$_2$)$_2$N, OH on C-C with CH$_3$, H, R$_4$ | (C$_6$H$_5$CH$_2$)$_2$N, OH isomer with CH$_3$, R$_4$ |
|---|---|---|---|---|
| CH$_3$MgI | 87 | —CH$_3$ | 5 | 95 |
| CH$_3$Li | 91 | —CH$_3$ | 9 | 91 |
| CH$_3$Ti(OC$_3$H$_7$i)$_3$ | 78 | —CH$_3$ | 3 | 97 |
| C$_6$H$_5$MgBr | 85 | —C$_6$H$_5$ | 3 | 97 |
| C$_2$H$_5$MgBr | 85 | —C$_2$H$_5$ | 5 | 95 |
| i-C$_3$H$_7$MgBr | 75 | -iC$_3$H$_7$ | <4 | >96 |
| tert. C$_4$H$_9$Li | 88 | -tert. C$_4$H$_9$ | <4 | >96 |
| (CH$_3$)$_2$Zn/TiCl$_4$ | 82 | —CH$_3$ | 94 | 6 |
| CH$_2$=C(OLi)(OCH$_3$) | 82 | —CH$_2$COOCH$_3$ | 5 | 95 |
| CH$_2$=C(OSi(CH$_3$)$_3$)(OCH$_3$) /BF$_3$ | 59 | —CH$_2$COOCH$_3$ | 4 | 96 |
| (CH$_3$)$_2$C=C(OLi)(OCH$_3$) | 84 | —C(CH$_3$)$_2$COOCH$_3$ | 3 | 97 |
| (CH$_3$)$_2$C=C(OTi(OC$_3$H$_7$i)$_3$)(OCH$_3$) | 72 | —C(CH$_3$)$_2$COOCH$_3$ | 4 | 96 |
| (CH$_3$)$_2$C=C(OTi(N(C$_2$H$_5$)$_2$)$_3$)(OCH$_3$) | 73 | —C(CH$_3$)$_2$COOCH$_3$ | 3 | 97 |

TABLE 2

| Agent | Yield [% of theory] | R$_4$ | (C$_6$H$_5$CH$_2$)$_2$N, OH on C-C with C$_6$H$_5$—CH$_2$, H, R$_4$ | isomer with C$_6$H$_5$—CH$_2$, R$_4$ |
|---|---|---|---|---|
| CH$_3$MgI | 85 | —CH$_3$ | 8 | 92 |
| CH$_3$Li | 86 | —CH$_3$ | 11 | 89 |
| CH$_3$Ti(OC$_3$H$_7$i)$_3$ | 89 | —CH$_3$ | 7 | 93 |
| C$_6$H$_5$MgBr | 84 | —C$_6$H$_5$ | 3 | 97 |
| CH$_2$=CHCH$_2$MgCl | 82 | —CH$_2$CH=CH$_2$ | 28 | 72 |
| CH$_2$=CHCH$_2$Ti(OC$_3$H$_7$i)$_3$ | 84 | —CH$_2$CH=CH$_2$ | 12 | 88 |
| CH$_2$=CHCH$_2$Ti[N(C$_2$H$_5$)$_2$]$_3$ | 81 | —CH$_2$CH=CH$_2$ | 7 | 93 |
| (CH$_3$)$_2$Zn/TiCl$_4$ | 63 | —CH$_3$ | 78 | 22 |
| CH$_2$=CHCH$_2$Si(CH$_3$)$_3$/SnCl$_4$ | 79 | —CH$_2$CH=CH$_2$ | 87 | 13 |
| C$_6$H$_5$CH$_2$CH$_2$MgCl | 84 | —CH$_2$CH$_2$C$_6$H$_5$ | 3 | 97 |
| C$_6$H$_5$≡CLi | 72 | —C≡CC$_6$H$_5$ | 2 | 98 |
| (CH$_3$)$_3$SiCN/BF$_3$ | 74 | CN | 5 | 95 |
| (CH$_3$)$_3$SiCN/ZnBr$_2$ | 79 | CN | 5 | 95 |
| (CH$_3$)$_3$SiCN/MgBr$_2$ | 76 | CN | 78 | 22 |
| (CH$_3$)$_3$SiCN/TiCl$_4$ | 59 | CN | 78 | 22 |

TABLE 3

| Agent | Yield [% of theory] | R$_4$ | (C$_6$H$_5$CH$_2$)$_2$N, OH on C-C with (CH$_3$)$_2$CH—CH$_2$, H, R$_4$ | isomer with (CH$_3$)$_2$—CH—CH$_2$, R$_4$ |
|---|---|---|---|---|
| CH$_5$MgI | 85 | —CH$_3$ | 10 | 90 |

TABLE 3-continued

| Agent | Yield [% of theory] | R4 | $(C_6H_5CH_2)_2N\diagdown\;\;\diagup OH$ <br> $H\blacktriangleright C-C$ <br> $(CH_3)_2CH-CH_2\;\;\;\;H\;\;\;R_4$ | $(C_6H_5CH_2)_2N\diagdown\;\;\diagup OH$ <br> $H\blacktriangleright C-C\blacktriangleleft H$ <br> $(CH_3)_2-CH-CH_2\;\;\;\;\;\;R_4$ |
|---|---|---|---|---|
| CH₃Li | 89 | —CH₃ | 20 | 80 |
| CH₃Ti(OC₃H₇i)₃ | 80 | —CH₃ | 6 | 94 |
| C₆H₅MgBr | 84 | —C₆H₅ | 3 | 97 |
| CH₂=CHCH₂Si(CH₃)₃/SnCl₄ | 78 | —CH₂CH=CH₂ | 90 | 10 |
| CH₂=C(OLi)(OC₂H₅) | 75 | —CH₂COOC₂H₅ | 10 | 90 |
| CH₂=C(OSi(CH₃)₃)(OC₆H₅) /MgBr₂ | 60 | —CH₂COOC₆H₅ | 88 | 12 |

TABLE 4

| Agent | Yield [% of theory] | R4 | $(C_6H_5CH_2)_2N\diagdown\;\;\diagup OH$ <br> $H\blacktriangleright C-C$ <br> $(CH_3)_2CH\;\;\;\;H\;\;\;R_4$ | $(C_6H_5CH_2)_2N\diagdown\;\;\diagup OH$ <br> $H\blacktriangleright C-C\blacktriangleleft H$ <br> $(CH_3)_2CH\;\;\;\;\;\;R_4$ |
|---|---|---|---|---|
| CH₃MgI | 87 | —CH₃ | 5 | 95 |
| C₆H₅MgBr | 69 | —C₆H₅ | 9 | 91 |
| CH₂=CHCH₂Ti[N(C₂H₅)₂]₃ | 83 | —CH₂CH=CH₂ | 4 | 96 |
| CH₂=CHCH₂SI(CH₃)₃/SnCl₄ | 78 | —CH₂CH=CH₂ | 95 | 5 |

EXAMPLE 2

(a) 1.0 g (=6.1 mmol) of phenylalanine, 3.6 g (=24 mmol) of K₂CO₃ in 20 ml of H₂O and 2.4 g (=20 mmol) of allyl bromide are stirred under reflux for 0.5 hours. The reaction mixture is then cooled and extracted with ethyl acetate. The organic phase is washed with brine and then concentrated in a rotary evaporator. The residue which, according to thin-layer chromatography, is a homogeneous product is purified by chromatography on a silica gel column (PE/EtOAc; 98:2). 1.2 g (=70% of theory) of allyl S-2-(N,N-diallylamino)-β-phenolpropionate are obtained in the form of a colourless oil.

(b) A solution of 1.31 g (=4.56 mmol) of allyl S-2-(N,N0-diallylamino)-3-phenylpropionate in 5 ml of ether is added dropwise to a suspension of 0.23 g (=5.93 mmol) of lithium aluminium hydride in 10 ml of ether while stirring and cooling at 0° C. After addition is complete, the cooling bath is removed, and the reaction mixture is stirred at room temperature for 2 hours. The reaction mixture is then hydrolised by the successive addition of 0.23 ml of H₂O, 0.23 ml of 15% strength sodium hydroxide solution and 0.69 ml of H₂O. The resulting hydroxides are filtered off, extracted by boiling twice with ether, treated with aqueous sulphuric acid and again extracted with ether. The combined extracts are washed with NaCl/H₂O, dried over magnesium sulphate and concentrated in vacuo. The residue is purified by chromatography on a silica gel column (PE/EtOAc; 95:5). 0.64 g(=61% of theory) of S-2-(N,N-diallylamino)-3-phenylpropanol is obtained in the form of a colourless oil.

(c) 236 mg (=3.0 mmol) of dimethyl sulphoxide are added dropwise to a solution of 0.24 g (=1.8 mmol) of oxalyl chloride in 20 ml of methylene chloride which has been cooled to −60° C. The solution is stirred for 5 minutes, and then 246 mg (=0.75 mmol) of S-2-(N,N-diallylamino)-3-phenylpropanol in 3 ml of methylene chloride are added dropwise. After 45 minutes, 610 mg (6.0 mmol) of triethylamine are added. The mixture is stirred for 40 minutes and then first treated with H₂O and then extracted with 20 ml of methylene chloride. The organic phase is separated off, washed with H₂O and dried over MgSO₄. After removal of the solvent, 297 mg (=85% of theory) of S-2-(N,N-diallylamino)-3-phenylpropanal are obtained in the form of a colourless oil.

(d) A solution of 300 mg (=1.3 mmol) of S-2-(N,N-diallylamino)-3-phenylpropanal in 1 ml of ether is added dropwise to a solution of 1.4 mmol of methyllithium in 20 ml of ether at −10° C. After the reaction mixture has been stirred for 1 hour it is hydrolysed by addition of 4 ml of saturated ammonium chloride solution; the organic phase is separated off, and the aqueous phase is extracted with ether. The combined organic phases are dried over Na₂SO₄, and then the solvent is removed in vacuo. The residue is purified by chromatography on a silica gel column (PE/EtOAc; 96:4). 260 mg (=81% of theory) of (2S,3R)-2-(N,N-diallylamino)-1-phenyl-3-butanol are obtained as an oil. The determination of the diastereoselectivity by ¹³C NMR spectroscopy showed a diastereomeric ratio of 87:13.

EXAMPLE 3

121 mg (=1.21 mmol) of trimethylsilyl cyanide are added, at −20° C. with stirring, to a suspension of 350 mg (1.06 mmol) of the S-2-(N,N-dibenzylamino)-3-phenylpropionaldehyde described in Example 1 bβ) and 271 mg (=1.2 mmol) of zinc bromide in 10 ml of methylene chloride. After the reaction mixture has been stirred for 3 hours it is treated with 5 ml of H₂O. The organic phase is separated off, and the aqueous phase is extracted with ether. The combined organic phases are washed with brine and dried over MgSO₄. The O- silylated cyanohydrin resulting after removal of the solvent is desilylated by treatment with 10% strength aqueous solution of citric acid. The crude product is purified by chromatography (silica gel; PE/EtOAc; 50:50). 283 mg (=75% of theory) of (2S,3S)-3-(N,N-dibenzylamino)-2-hydroxy-4-phenyl-butanenitrile are obtained.

If MgBr$_2$ is used in place of ZnBr$_2$ as Lewis acid, then 220 mg (=61% of theory) of (2R,3S)-3-(N,N-dibenzylamino-2-hydroxy-4-phenylbutanenitrile are obtained.

EXAMPLE 4

300 mg (=1.02 mmol) of the S-2-(N,N-dibenzylamino)-4-methyl-pentanal described in Example 1 b8) are added, at −15° C. with stirring, to a suspension of 206 mg (=1.2 mmol) of MgBr$_2$ in 10 ml of methylene chloride. After 20 minutes, 253 mg (=1.22 mmol) of 1-phenoxy-1-trimethylsiloxyethylene are added dropwise; the mixture is stirred for 12 hours and then poured onto 5 ml of H$_2$O. The mixture is treated with a mixture of aqueous HF/THF, and is extracted several times with ether. The combined organic phases are washed with H$_2$O, dried over MgSO$_4$ and concentrated in vacuo. The oil remaining as residue is purified by chromatography. 180 mg (=62% of theory) of phenyl 4-(N,N-dibenzylamino)-3-hydroxy-6-methylheptanecarboxylate are obtained (diastereomer ratio 3S,4S:3R,4S=78:22).

What is claimed is:

1. An optically active α-amino aldehyde of one of the formulae

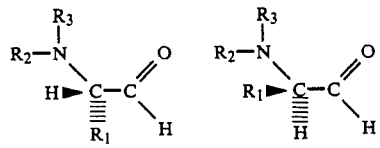

in which

R$_1$ is unsubstituted C$_1$–C$_{12}$ alkyl, C$_1$–C$_{12}$ alkyl substituted by amino, hydroxyl, benzyloxy, benzylmercapto, a carbamoyl group, an imidazolyl-4 group, or an indolyl-3 group, vinyl, unsubstituted benzyl, benzyl substituted by C$_1$–C$_4$-alkyl, C$_1$–C$_4$-alkoxy, benzyloxy, or halogen, unsubstituted phenyl, or phenyl substituted by hydroxyl, C$_1$–C$_4$-alkyl or C$_1$–C$_4$-alkoxy, wherein said R$_1$ is not alkyl substituted by hydroxyl and at the same time by three benzyloxy groups, and R$_2$ and R$_3$ are an unsubstituted benzyl group or a substituted benzyl group, or together form an unsubstituted phenylene-(1-2)-bis-methylene group or a substituted phenylene-(1,2)-bis-methylene group, or R$_2$ is an unsubstituted benzyl radical or a substituted benzyl radical, wherein the substituents for the substituted benzyl and substituted phenylene-(1, 2-bis-methylene are C$_1$–C$_4$-alkyl, C$_1$–C$_4$-alkoxy, benzyloxy, or halogen.

2. An optically active alpha-amino aldehyde according to claim 1, wherein said aldehyde is S-alpha-(N,N-dibenzyl-amino) propionaldehyde.

3. An optically active alpha-amino aldehyde according to claim 1, wherein the C$_1$–C$_{12}$ alkyl is methyl, ethyl, iso-propyl, butyl, sec.-butyl, amyl or hexyl.

4. An optically active alpha-amino aldehyde according to claim 1, wherein the substituted alkyl is benzyloxymethyl, benzylthiomethyl, 1-benzyloxyethyl, 2-methylthioethyl, carbamoylethyl, 2-carbamoylethyl, 3-(N,N-dibenzylamino)-propyl, 4- (N,N-dibenzylamino) butyl, (imidazoly-4)-methyl or (indolyl-3)-methyl.

* * * * *